United States Patent [19]

Tammisalo et al.

[11] Patent Number: 4,646,335
[45] Date of Patent: Feb. 24, 1987

[54] APPARATUS FOR X-RAY PHOTOGRAPHY OF THE AREA OF THE DENTITION AND OF THE JAWS

[75] Inventors: Erkki Tammisalo; Heikki Kanerva, both of Turku; Jaakko Aarnio, Helsinki; Markku Wederhorn, Espoo; Kai Laner, Helsinki, all of Finland

[73] Assignee: Orion-Yhtyma, Helsinki, Finland

[21] Appl. No.: 696,691

[22] Filed: Jan. 31, 1985

[30] Foreign Application Priority Data

Jan. 2, 1984 [FI] Finland ................................ 840413

[51] Int. Cl.$^4$ .............................................. A61B 6/14
[52] U.S. Cl. ..................................... 378/38; 378/40; 378/196; 378/197
[58] Field of Search ..................... 378/38, 39, 40, 196, 378/197, 20; 74/422

[56] References Cited

U.S. PATENT DOCUMENTS

| | | | |
|---|---|---|---|
| 3,670,163 | 6/1972 | Lajus .................................. | 378/196 |
| 3,803,418 | 4/1974 | Holstrom .......................... | 378/196 |
| 4,145,611 | 3/1979 | Välilä ................................. | 378/40 |
| 4,541,293 | 9/1985 | Caugant et al. ...................... | 74/422 |

*Primary Examiner*—Craig E. Church
*Assistant Examiner*—John C. Freeman
*Attorney, Agent, or Firm*—Ladas & Parry

[57] ABSTRACT

An apparatus for panoramic X-ray photography of the area of the dentition and the jaws, comprising a frame part, a bearing part linearly movable in relation to the frame part, and a support arm attached rotatably to the bearing part, and having at one end an X-ray film and at the opposite end an X-ray source. The movements of the bearing part, the support arm and the film are synchronized in such a way that an image of an area of desired shape, e.g. the patient's dental arch, is obtained on the film. The invention provides the effect that the X-ray beam can be tilted to a desired angle in relation to the horizontal, whereby it is possible with greater sharpness to photograph, for example, teeth slanted in relation to the vertical. For this purpose, the support arm is tiltable about an axis perpendicular to its rotational axis so that, when this axis is vertical, the straight line connecting the source of radiation and the film is obligue to the horizontal. The structural parts between the bearing part and the support arm are provided with co-operating curved guide means, the mutual movement of which alters the tilt position of the support arm. The control movements are performed by stepping motors.

10 Claims, 2 Drawing Figures

APPARATUS FOR X-RAY PHOTOGRAPHY OF THE AREA OF THE DENTITION AND OF THE JAWS

BACKGROUND OF THE INVENTION

1. The present invention relates to an apparatus for X-ray photography of the area of the dentition and of the jaws, and of the type comprising a stationary frame part, a bearing part which is movably mounted to the frame part and preferably performs a linear movement, and a support arm which is rotatably attached using bearings to the bearing part and has at one end a source of X-ray radiation and at the opposite end a movable X-ray film, the movements of the bearing part, the support arm and the film being synchronized in such a way that a sharp image of only an area of the desired shape is obtained on the film, for example the area of the patient's dental arch.

2. Description of the Prior Art

In panoramic X-ray photography it is known, in order to obtain a sharp image of the dental arch, to allow the rotational axis of the support arm to move during the exposure in a predetermined manner linearly or non-linearly in such a way that this movement is dependent on the angular position of the support arm at each given time. The movement of the rotational axis may be linear, and parallel to the axis of symmetry of the dental arch, perpendicular to it, curved, or non-continous between predetermined points. The enlargement can be adjusted by shifting the location of the patient, i.e. the head-supporting devices, in relation to the support arm.

In spite of the above-mentioned movement combinations and adjustments, the image obtained is not always as sharp as would be desired, especially when some specific part of the dental arch is concerned. It is evident that it is not always possible by means of adjustments to compensate for the variation is the dentition among defferent patients. For example, a situation in which the axis of the rotational movement of the support arm is vertical and the position of at least some of the teeth deviates from the vertical, causes certain blur in the image.

SUMMARY OF THE INVENTION

It is therefore, an object of the present invention to expand and further improve the adjustment possibilities. The object is in particular to provide such a possibility for tilting the support arm that it will be possible to photograph sharply teeth which are slanted in relation to the vertical plane, without having to change the position of the patient.

In order to achieve this object the support arm is connected to the bearing part by mediation of structural parts which enable the support arm to be tilted about an imaginary axis of inclination, the tilting axis being situated at the level of the patient's head and being perpendicular to the rotational axis, the rotational axis retaining its direction regardless of the tilting.

By tilting the support arm according to the invention it is possible to photograph sharply a patient's tooth which is at an angle to the vertical plane. It is evident that in such a case the reach of the beam is also preferably limited in the vertical direction in such a way that only the upper teeth or the lower teeth are photographed. When necessary, and according to the situation at each given time, the adjustments mentioned above can, of course, be carried out continuously also during the exposure. Especially today, when the use of a separate stepping motor for each adjustment is becoming established, the stepping motors being processor controlled according to a predetermined program or predetermined programs, several mutually synchronized adjustments such as these are quite easy to implement.

In order to diversify the possibilities for adjustment, according to one additional characteristic of the invention it has been arranged so that the support arm, and at the same time the source of radiation and the X-ray film, can be moved in a direction parallel to the plane of the X-ray beam. By means of this support-arm movement in a direction parallel to the beam, i.e. to the straight line connecting the source of radiation and the film, it is easy to select the enlargement ratio for the image. When further arrangements are made for the support arm to be able to make a complete rotation, it is possible to allow the source of radiation to pass around either the neck or the face of the patient, without the patient being moved between the operations.

DESCRIPTION OF THE PREFERRED EMBODIMENTS

Figure 1:
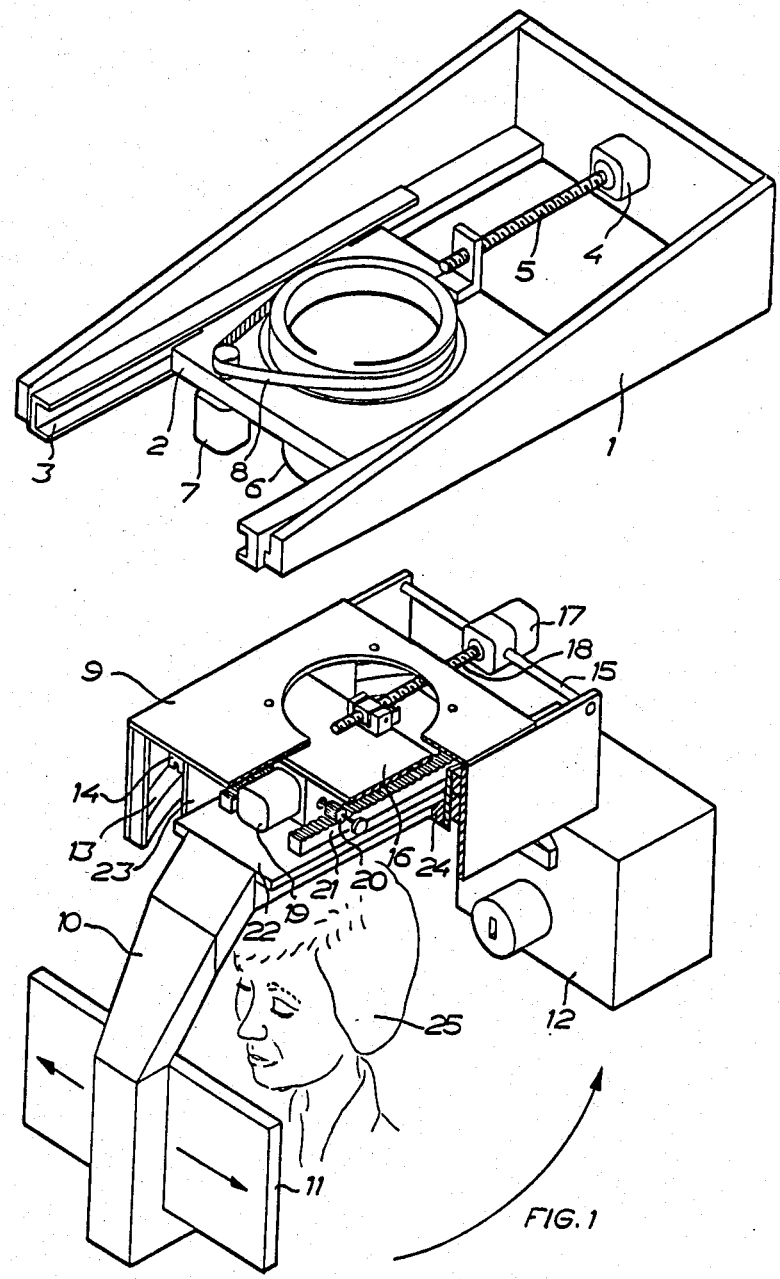
FIG. 1 depicts a perspective representation of one embodiment of the X-ray photography apparatus according to the invention, in part exploded for the sake of illustration.

The X-ray apparatus includes a stationary frame, which is indicated in the drawing by reference numeral 1 and which, in addition to the part shown in the drawing, normally includes a vertical pole attached to it and a stand resting on the floor. The protruding part 1 shown in the drawing is, of course, in practice encased, but for the sake of illustration this casing is not shown.

To the frame 1 there is attached using bearings a bearing part 2, which is capable of moving in the frame linearly along a horizontal plane and supported by rails 3. The movement is produced by a stepping motor 4, the shaft of which is a screw 5 which works in conjunction with the bearing part 2. To the bearing part 2 there is further attached rotatably with bearings a sleeve 6, which is rotatedby another stepping motor 7 by transmission of a cogged belt 8.

To the sleeve 6 there is fastened by means of screws a casing-like part 9, which thus rotates together with the sleeve 6 and to which there is further attached with bearings in a manner depicted below a support arm 10, which constitutes an essential part of the photography apparatus.

At one end of the support arm there is a movable X-ray film 11 and at its opposite end source 12 of X-radiation with means for limiting the beam. During the exposure the support arm 10 performs at least a partial totational movement, the fulcrum moving at the same time linearly together with the bearing part 2, and the head of the patient being located between the source 12 of X-radiation and the X-ray film 11. This arrangement is already so familiar to an expert in the art that it is not described here in greater detail. It is also evident that, as an alternative to the linear shift of the bearing part 2, it is possible to shift the patient, i.e. the chair of the patient, correspondingly during the rotational movement of the support arm.

It is an essential characteristic of the present invention that a possibility is provided for tilting the support arm in such a way that the X-ray beam travels obliquely upwards or obliquely downwards. In addition, a possibility is provided for moving the support arm in the direction of the arm itself, in other words in a direction parallel to the straight line connecting the source of X-radiation and the film. The last-mentioned movements are implemented as follows.

At the lower edge of the interior sides of the casing part 9 there are provided curved guides 13, which work in conjunction with corresponding curved guides 14 in the control part 16. The lower edge of the side piece 23 of the control part 16 has additionally a strip 24, the flat middle section 22 of the support arm 10 being capable of moving supported by the strip. The last-mentioned movement in a direction parallel to the X-ray beam is produced by a stepping motor 19, which rotates a transverse shaft and its cogwheels 20, the cogwheels for their part working in conjunction with cogged bars 21 in the middle section 22. The control part 16 for its part is moved by a screw 18 which grips it in an articulated way, the screw serving as the shaft of the stepping motor r7, which for its part is articulated to the casing part 9 by means of a transverse shaft 15. The motor 17 thus affects the mutual transfer of the guides 13 and 14, and since the guides are curved, the transfer motor 17 of the control part 16 has been suspended in an articulated way.

The image enlargement coefficient can be changed by moving the support arm 10 in a direction parallel to the beam, in other words by means of the motor 19. By rotating the support arm 10 180° it is thus possible to allow the source of radiation to travel around either the neck or the face of the patient, and a suitable enlargement coefficient can be produced without shifting the patient.

For example, when somewhat slanted teeth are photographed, it may be appropriate to tilt the support arm by means of the motor 17 and the curved rails 13, 14 in the manner described above, at which time it is, of course, advisable also to limit the X-ray beam in the vertical direction by means of a suitable collimator so that the teeth of only the upper jaw or the lower jaw are photographed. By means of the arrangement according to the figure, in which the axis of tilting is approximately at the level of the head of the patient 25, the effect is produced that the tilting does not substantially alter the distance of the source of radiation, respectively the film, from the patient, which would occur if the tilting were produced by means of a horizontal transverse axis. In other words, according to the present invention, the distance of the source and the film to the object remains essentially constant regardless of the described tilting.

Figure 2:
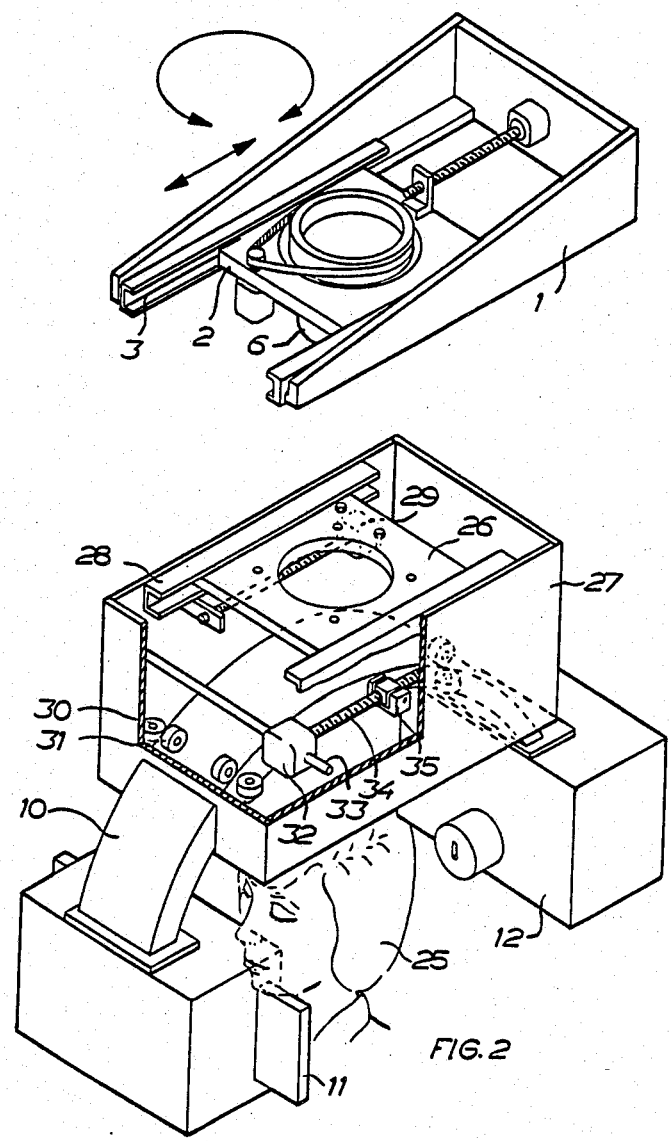
FIG. 2 depicts in a corresponding manner an alternative embodiment.

One alternative arrangement is shown in FIG. 2. In FIG. 2, there is a stationary frome as described previously and the linear transfer, i.e. the transfer in a direction parallel to the plane of the X-ray beam, is produced by means of a plate 26 attached to the sleeve 6, the edges of the plate being guided by rails 28 on the sides of the casing-like part 27. The transfer is effected by means of a motor 29, which is secured to the lower surface of the plate 26.

In this embodiment, at least the middle section of the support arm 10 is curved in such a way that the center point of the curve, i.e. the tilting axis, is again located approximately at the level of the head of the patient 25. Rollers 30, 31, attached by means of bearings inside the casing 27, work in conjunction with the arch 10, the rollers working against the side, upper and lower surfaces of the arch (the last-mentioned not shown), directing the arch along its own curved line. The transfer movement is produced by means of a spindle motor 32 attached turnably to the casing 27 by means of a shaft 33, the threaded shaft 34 of the motor engaging in a mating piece 35 attached turnably to the side of the arch.

As is well known by experts in the field, the film must also be moved synchronically with the rotational movement of the support arm. The shifting of the film is also produced preferably by means of a stepping motor, although this arrangement is not shown in the drawing. As was mentioned above, stepping motors are preferably controlled electronically in a manner known per se, especially by means of a programmed or a programmable microprocessor, in which case no mechanical means such as cams or the like are required for mutual synchronization of the movements of the different parts.

What we claim is:

1. An apparatus for X-ray photography of the area of dentition and the jaws, said apparatus comprising
   a stationary frame part;
   a bearing part supported in the frame part and movable in relation thereto;
   a support arm mounted for rotational movement in relation to said bearing part;
   a source of means for rotating said arm for X-rays provided at one end of the support arm;
   a movable X-ray film provided at the other end of the support arm; the movements of the support arm and the film being synchronized so that, during the movement, an image of an area of desired shape, e.g., is obtained on the film;
   structural parts for mounting the support arm in relation to the bearing part;
   means provided in said structural parts and enabling the support arm to be tilted about an axis, said axis being located at the level of the patient's head and being perpendicular to the axis of rotation.

2. An apparatus according to claim 1, wherein the middle section of the support arm, or a part attached to it, is provided with curved guides serving as tilting means.

3. An apparatus according to claim 2, wherein the support arm is suspended from a sleeve or the like, attached by means of bearings rotatably to the bearing part, the sleeve being attached to a first structural part having on two sides guide rails which are convex as seen from the side and which serve to support and to tilt the support arm, the middle section of the support arm being provided with corresponding curved rails or being connected to a second structural part provided with such rails.

4. An apparatus according claim 3, wherein said second structural part provided with the mating rails is movable by means of a motor articulated to the first structural part attached to the sleeve, a threaded shaft of the motor engaging in a mating piece articulated to the second structural part provided with rails.

5. An apparatus according to claim 3, wherein the second structural part provided with mating rails is supported by the curved rails of the first structural part attached to the sleeve, the second structural part allowing the support arm to be adjusted in relation thereto in a direction parallel to the plane of the X-ray beam.

6. An apparatus according to claim 5, wherein the second structural part having curved mating rails is further provided with two straight parallel rails, on which the side edges of a middle section of the support arm are guided, the second structural part being also provided with friction wheels or cogwheels rotated by a motor, and the middle section of the support arm having rails or cogged bars, parallel to the edges and cooperating with said wheels.

7. An apparatus according to claim 2, wherein the middle section of the support arm is curved and a casing-like structural part connected to the bearing part has guide rollers or the like cooperating with the curved support arm, the guide rollers guiding the support arm along a curved line.

8. An apparatus according to claim 7, wherein the transfer of the curved support arm is effected by means of a spindle motor attached by means of bearings turnably to the casing-like structural part, the threaded shaft of the motor engaging in a threaded mating piece in the support arm.

9. An X-ray apparatus according to claim 7 wherein the casing-like structural part is additionally guided in the bearing part in such a way that it can move rectilinearly, as seen from above, in a direction parallel to the support arm.

10. An X-ray apparatus according to claim 9, wherein the support arm is suspended from a sleeve or the like, which is attached rotatably to the bearing part, and wherein a plate-like part which is guided by rails on the sides of the casing-like structural part is attached to the sleeve.

* * * * *